United States Patent
Hugueny et al.

(10) Patent No.: US 6,425,910 B1
(45) Date of Patent: Jul. 30, 2002

(54) FORCEPS, IN PARTICULAR BIOPSY FORCEPS

(75) Inventors: Jean-Marie Hugueny, Regnie-Durette; Jean-Louis Sabin, Sainte-Luce; Pierre Jean-Claude Sabin, Bois Guillaume; Antoine Warnier, Paris, all of (FR)

(73) Assignee: Eurobiopsy, Quincie (FR)

( * ) Notice: Subject to any disclaimer, the term of this patent is extended or adjusted under 35 U.S.C. 154(b) by 0 days.

(21) Appl. No.: 09/463,941

(22) PCT Filed: Aug. 7, 1998

(86) PCT No.: PCT/FR98/01777

§ 371 (c)(1),
(2), (4) Date: Feb. 4, 2000

(87) PCT Pub. No.: WO99/07287

PCT Pub. Date: Feb. 18, 1999

(30) Foreign Application Priority Data

Aug. 7, 1997 (FR) .............................................. 97 10156

(51) Int. Cl.$^7$ .............................................. A61B 17/28
(52) U.S. Cl. ...................................................... 606/206
(58) Field of Search ........................ 606/205–211, 157, 606/151, 184; 600/564, 566, 567

(56) References Cited

U.S. PATENT DOCUMENTS

| 5,052,402 A | * | 10/1991 | Bencini et al. ............. 600/564 |
| 5,562,102 A | | 10/1996 | Taylor |
| 6,123,678 A | * | 9/2000 | Palmer et al. .............. 600/567 |

FOREIGN PATENT DOCUMENTS

| EP | 0380874 | 8/1990 |
| EP | 05738173 | 12/1993 |

* cited by examiner

Primary Examiner—Kevin Truong
(74) Attorney, Agent, or Firm—Greenblum & Bernstein, P.L.C.

(57) ABSTRACT

Forceps instrument comprising a sheath having a first end and an elongated maneuvering element slidably disposed in the first end of said sheath. The sheath has an axis. The instrument comprises two jaw-pieces, at least one of the jaw-pieces being movable away from and toward the other of the jaw-pieces when the maneuvering element slides axially in the first end of the sheath. The jaw-pieces have, in an extension of a part thereof, an arm extending progressively toward the axis of the sheath so as to form a first, internal, inclined surface extending progressively toward the axis and facing the latter and a second, external, inclined surface extending progressively toward the axis and facing the internal surface of the sheath. The arm has a convex excrescence which is slidable substantially against the internal surface of the sheath, the excrescence having a concave hollow cavity facing the axis. The sheath has, near its end beyond which the jaws extend, a transverse element against which the internal surface of the arm slides. The elongate maneuvering element terminates in a head housed in the concave hollow cavity so that, when the elongate maneuvering element is moved toward a free end of the sheath, it pushes the jaw-pieces back beyond the end of the sheath, thus causing the internal surface of the arm, which slides over the transverse element, to pivot by a ramp effect, moving the at least one jaw of the jaw-pieces away from the other jaw, the movement away being permitted by the inclination of the external surface which protrudes from the end of the internal surface of the sheath. The excrescence of the arm pivoting, during this movement, about the head while still being guided in the sheath, reverse movement of the maneuvering element causing the jaw-pieces to move closer by a reverse movement. The transverse element includes a passage having an axis substantially parallel to the axis of the sheath for accommodating an auxiliary tool between the two jaw-pieces.

19 Claims, 5 Drawing Sheets

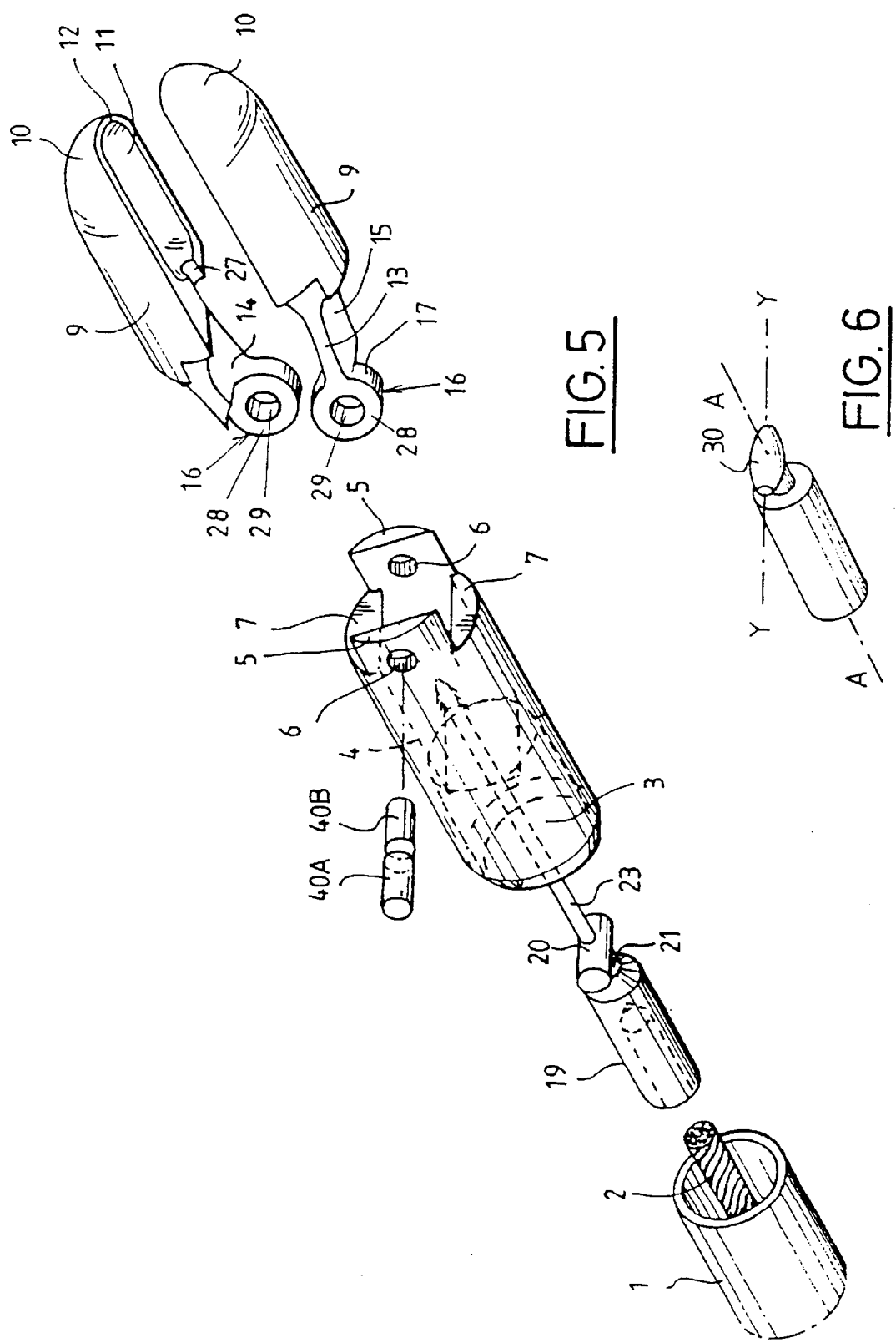

FORCEPS, IN PARTICULAR BIOPSY FORCEPS

CROSS REFERENCE TO RELATED APPLICATIONS

The present application is the U.S. National Phase of PCT/FR98/01777.

BACKGROUND OF THE INVENTION

1. Field of the Invention

The present invention relates to a forceps device, such as, a biopsy forceps, that is to say, a forceps having two jaw-pieces capable of being moved away from each other, of being moved closer to each other and, while they are moving closer to each other, of cutting or detaching a specimen of body tissue which is seized between the two jaw-pieces of the forceps and which can subsequently be recovered outside the body.

The invention also extends to other instruments which can be used in medicine or in surgery, such as, for example, forceps instruments having no cutting effect, for providing a clamping effect, or retractors, or else scissors for surgical use, or any other instrument of this kind having two elements, at least one of which is capable of being moved away from and of being moved toward the other.

2. Discussion of the Background Information

The currently known biopsy forceps have two jaw-pieces capable of being moved away from each other or moved closer to each other, these being articulated on the end of an elongate, rigid or flexible tube, or sheath inside which a cable can slide. The cable is being provided at its other end with means for it to be maneuvered by the operator. These devices have articulated links designed to amplify movement between the control means formed by the cable and the jaw-pieces proper.

These forceps are mechanically complex and consist of at least about ten components. They are therefore expensive, difficult to fit and subject to wear and failures. At the linkage to the cable, they lead to torsional effects inducing fatigue in the cable which may cause it to break. Other components, too, may be exposed to excessive stresses, so that in the final analysis these forceps have a large number of drawbacks.

Moreover, the presence of the links, an articulation end of which extends along the axis of the forceps, makes it hard to add an auxiliary tool such as a barb extending along the axis of the forceps. Furthermore, it is extremely difficult to co-ordinate the movement of displacing the barb with the movement of opening the jaw-pieces of the forceps.

SUMMARY OF THE INVENTION

The present invention aims to remedy these drawbacks and to provide a forceps instrument, in particular a biopsy forceps, of extremely simple design, having a very limited number of components, eliminating any excessive force capable of leading to wear of the components, and enabling complex movements to be made, if required, in a simple manner, while maintaining very great precision in the movements of the jaw-pieces and also making it easy to use an auxiliary tool along the axis of the forceps.

The subject of the invention is a forceps instrument, in particular of the biopsy-forceps type, comprising, on the end of a sheath, two jaw-pieces, one of which, at least one of which is capable of being moved away from and of being moved toward the other when a maneuvering element slides axially in the end of the sheath.

The sheath may be optionally rigid. An elongated maneuvering element, preferably a cable, may slide in the sheath. The jaw-piece or jaw-pieces are capable of being moved away from and of being moved toward each other and have, in the extension of a part of the jaw-pieces acting as the jaws proper, an arm. The arm goes progressively toward the axis of the sheath so as to form a first, internal, inclined surface, going progressively toward the axis and facing the latter. Further the arm has second, external, inclined surface, also going progressively toward the axis and facing the internal surface of the end of the sheath. The arm has a convex excrescence capable of sliding substantially against the internal surface of the end of the sheath. The excrescence has facing the axis, a concave hollow cavity, wherein the sheath has, near its end beyond which the jaw proper extends, a transverse element, such as a rod against which the internal surface of the arm slides. The elongate maneuvering element terminates in a head housed in the concave hollow cavity so that, when the elongate maneuvering element or cable is moved toward the free end of the sheath, it pushes the jaw-piece back beyond the end, thus causing the internal surface of the arm, which slides over the transverse element, to pivot by a ramp effect, moving the jaw of the jaw-piece away from the other. Movement away from the other jaw is allowed by the inclination of the external surface which protrudes from the end of the internal surface of the sheath, the excrescence of the arm pivoting, during this movement, about the head while still being guided in said the sheath. Reverse movement of the maneuvering element caused the jaw-piece to move closer by a reverse movement. The transverse element includes a passage having an axis substantially parallel to the axis of the sheath, to accommodate an auxiliary tool between the two jaw-pieces.

According to particular embodiments:

- the transverse element includes an interruption forming the passage and the transverse element is formed by two coaxial half-rods carried by the end of the sheath;
- the transverse element includes an orifice forming the passage, which orifice extends substantially perpendicular to the axis of the transverse element;
- the transverse element has two protuberances which are integral with the sheath and project from the internal surface of the end of the sheath;
- each protuberance delimits a ramp whose normal is directed toward the end of the sheath, each ramp being extended by a shoulder for the sliding of the internal surface of the arm;
- it includes an auxiliary tool passing through the passage of the transverse element;
- the head is extended along the axis A—A of the sheath by the auxiliary tool, which is secured to it, which tool is accommodated such that it can move in translation in the passage of the transverse element when the maneuvering element is moved in the sheath;
- the auxiliary tool is a rigid shaft tapered at its end and forming a barb;
- the shaft is screwed into a threaded hole in the head;
- the concave hollow cavity is substantially spherical and the head is a ball-and-socket joint;
- the concave hollow cavity is at least partially in the form of a channel and the head is substantially cylindrical;
- the jaws have reliefs on the outside designed for gripping a hollow object when said jaws are moved apart in the hollow object;
- the jaw-pieces are electrically insulated from the outer surface of the sheath and the jaw-pieces have means for connection to a source of potential;

the two jaw-pieces are electrically insulated from one another and have means for connection to sources of different potentials; and the head and the concave hollow cavity are spherical and form a ball-and-socket joint for the articulation of the jaw-pieces.

Preferably, the end of the sheath, in particular when the sheath is flexible, is formed by a rigid element fixed to one end of the sheath proper by one end of the rigid element, the other, free end of which supports the transverse element or rod, in two crenel-shaped extensions so that the geometrical axis of the rod is located near the bottoms of the crenels.

Preferably, the internal surface of the end of the sheath, or of its rigid end element, is planar, the internal and external surfaces of the arm or arms then being planar surfaces or geometrically cylindrical surfaces with a generatrix parallel to the internal surface of the end of the sheath and to the rod, and the external surface of the excrescence of the arm also being cylindrical.

Advantageously, the cross section of the end of the sheath, or of its rigid end element, delimits internally a rectangle, in particular a square, the internal surface of the end of the sheath, or of its rigid end element, being generated by one side of the rectangle.

Thus, by virtue of the invention, the internal surface of the jaw-piece arm may have a straight profile, or on the contrary, a profile which may vary, going progressively toward the axis of the sheath as it penetrates further into the sheath, thereby enabling the kinematics of the movement of the jaw-pieces away from each other to correspond to the shape of the ramp thus formed. The external face of the arms is also shaped when being moved closer to the axis, preferably so as to constantly slide on the end of the internal surface of the sheath and thus to avoid any free movement of the arm between the rod and the internal surface of the sheath.

Beyond the arm, the jaw-piece has the part forming the jaw proper, which may be of any shape suited to the desired use thereof.

The jaw of the jaw-piece may, for example, be produced in the form of a spoon having a cutting perimeter in the case of a biopsy forceps.

As a variant, the shape of the jaw may be that of a flat jaw-piece, for example in order to produce a gripping or clamping effect.

As another variant, the jaw may be in the form of a scissors cutting blade in order to produce a cutting instrument.

In general, the two jaw-pieces are symmetrical and undergo perfectly symmetrical movements with respect to a plane passing through the axis of the end of the sheath and the axis of the rod.

In a variant, one of the jaw-pieces may be produced so as to remain rotationally stationary and to undergo only a straight sliding movement while the other undergoes a sliding and pivoting movement with respect to the sheath.

During use, it may be desired for the jaw-piece, when moving away, also to move axially with respect to the element to be treated, for example, an organ. In this case, the sheath will remain stationary with respect to the organ to be treated and the maneuvering means, such as the cable, will undergo a translational movement in the sheath.

On the other hand, it may be desired for the jaw-pieces to undergo only a movement away from or toward the object or organ to be treated and, in this case, it is the maneuvering element which will remain stationary while the sheath will be moved translationally along this elongate maneuvering element.

For this purpose, the maneuvering element and the sheath include means which are designed to act, in turn, as means of holding one of the maneuvering element and the sheath in position with respect to the organ to be treated and as means of moving the other of these, respectively.

It will be understood that a forceps device has thus been produced which is mechanically very simple and which is composed of a very small number of components, namely the two jaw-pieces, the transverse rod, the head which terminates the sheath, and optionally a tubular section added onto the end of the sheath and forming the internal surface for guiding and receiving, on its end, the rod.

This results in easy assembly and dismantling, simple maintenance and almost complete freedom from the risks of breaking or of failure.

Other advantages and characteristics of the invention will appear on reading the following description, given by way of nonlimiting examples, and with reference to the appended drawings in which:

BRIEF DESCRIPTION OF THE DRAWINGS

FIG. 5 is an exploded perspective view of an alternative embodiment of the device according to the invention, FIG. 6 is a perspective view of an alternative embodiment of the end-fitting to which the jaw-pieces are articulated.

DETAILED DESCRIPTION OF THE PRESENT INVENTION

Figure 1:
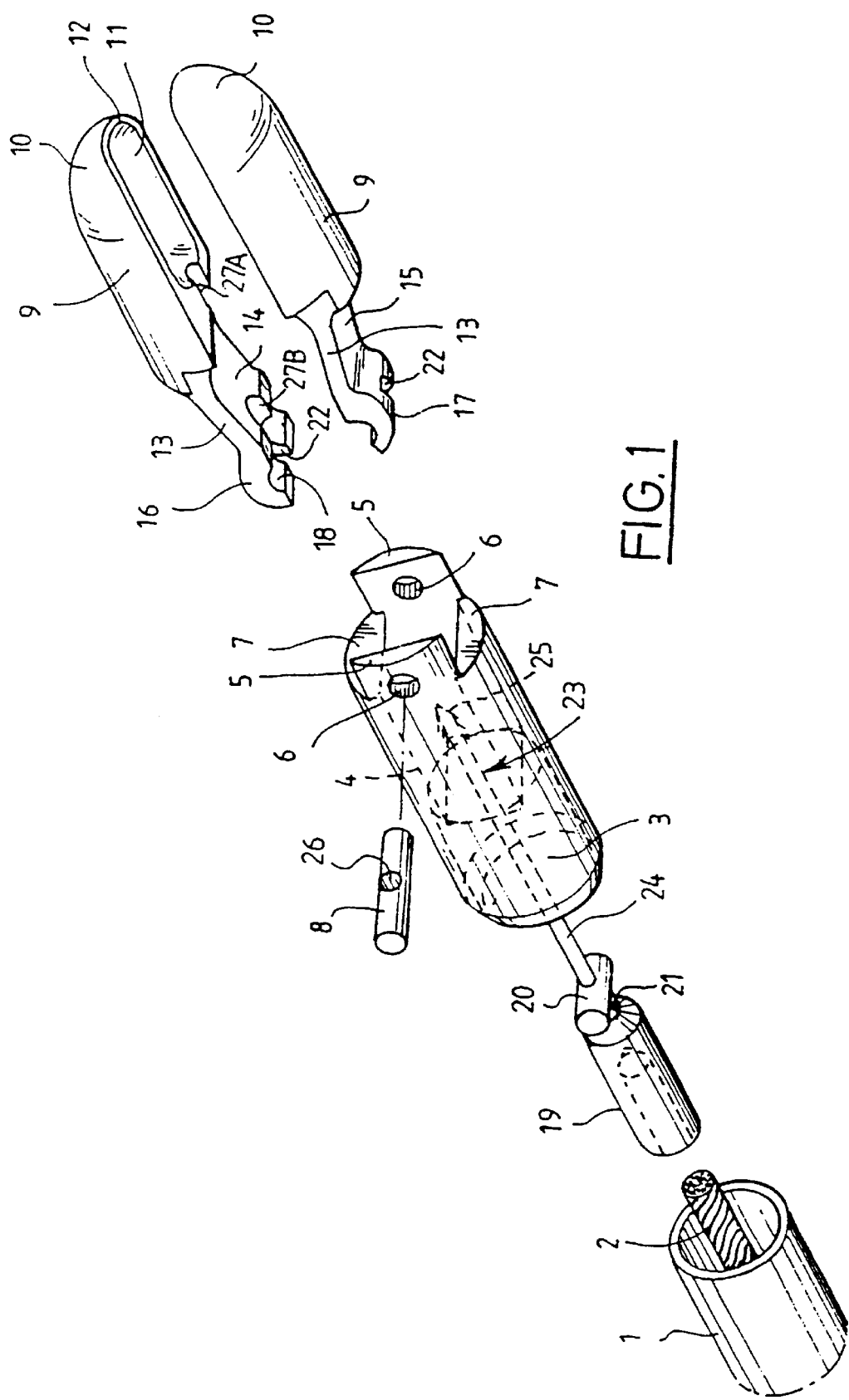
FIG. 1 is an exploded perspective view of the device according to the invention.

The biopsy forceps shown in the figures has an elongate sheath 1 inside which a semi-rigid cable 2 may move longitudinally, one of the ends, not shown, of which cable is connected to a maneuvering grip of the usual type in this kind of forceps. Advantageously, means are provided for holding one or other of the sheath and the cable in position with respect to the organ to be treated, and for moving whichever of the sheath and the cable is not being held.

The sheath 1 has, on its end, a metal tubular element 3, the outer surface of which is cylindrical, and which includes a central passage 4 of rectangular or square cross section. At its end remote from the sheath, the cylindrical component 3 is cut into the form of crenels so as to form two extensions 5 through which pass aligned holes 6, the common geometrical axis of which is located slightly above the plane of the two lowermost edges 7 of the crenels. Thus, the bottom part of the holes 6 lies substantially in the plane of these lowermost edges. A cylindrical rod 8 is forced into the holes 6, the rod thus extending transversely to the upper end of the square cross sectional passage 4.

The forceps has two identical jaw-pieces 9, whose parts which form the jaws proper 10 extend beyond the crenellate end of the tubular component 3 and have, in the usual manner, cavities 11 whose edges form a peripheral cutting lip 12. The jaw-pieces 9 are each extended, inside the component 3, by an arm 13 which passes between the rod 8 and the plane internal surface of the passage 4 facing the rod.

Figure 2:
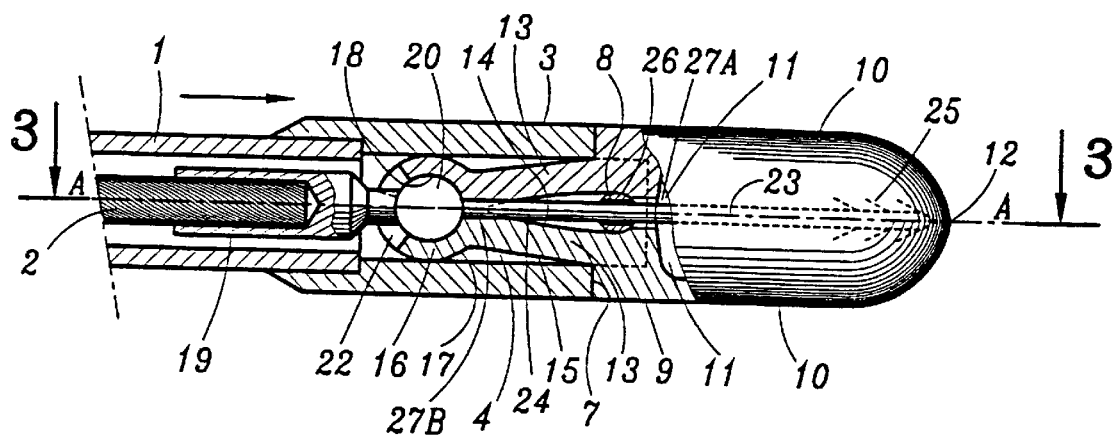
FIG. 2 is an axial sectional view of the device in a plane perpendicular to the rod.

The arm 13 has an internal surface 14 which is generated by a generatrix perpendicular to the plane of FIG. 2 and which, starting from the rod 8, goes progressively toward the axis A—A of the device until meeting this axis almost tangentially. Above the rod, in the position shown in FIG. 2, the surface 14 again curves in the direction of the axis, this time toward the top, so as substantially to surround the rod 8, as may be clearly seen in FIG. 2.

The arms 13 also have an outer surface 15 which also tends to move toward the axis A—A on going downward and which is such that the thickness of the arm 13, in the direction perpendicular to the axis A—A, lying in the plane of FIG. 2, tends to decrease progressively, this thickness being almost equal to the distance between the rod 8 and the plane internal wall of the component 3 at the edge 7.

The arm 13 has a convex end excrescence 16, the external surface 17 of which has substantially the shape of a cylinder having a circular base, the diameter of which is slightly less than the distance separating the two plane internal surfaces, facing each other, of the component 3. The excrescence 16 has, on the inside, a concave hollow cavity 18 which is not substantially spherical. This cavity 18 is, for example, formed, in the embodiment of FIGS. 1 to 4, by a channel extending along the axis of the cylinder delimiting the external surface 17. Thus, the axis of the channel delimiting the cavity 18 extends perpendicular to the axis A—A and parallel to the rod 8.

The end of the cable 2 carries an end-fitting 19 fixed to the cable and having, at its free end, a head 20 which is accommodated at the junction of the two cavities 18 of the two jaw-pieces 9.

The head 20 is not substantially spherical. It is substantially axisymmetric about a transverse axis Y—Y perpendicular to the axis A—A. It is, for example, formed by a cylindrical head extending perpendicular to the end of the end-fitting 19. The cylindrical head 20 is formed at the end of a shaft 21 of smaller diameter than the head 20 and which extends the end-fitting 19 axially.

The concave hollow cavity 18 intended to receive the cylindrical head 20 is then formed by two channels of semicylindrical cross section, the generatrix of which extends parallel to the rod 8. The sidewall of each channel extends in section over about 145°.

Notches 22 are formed axially at the ends of the excrescences 16. These notches 22 extend perpendicular to the channels 18 and are intended for the shaft 21 to pass through when the excrescences 16 enclose the head 20.

The forceps also has an axial auxiliary tool 23, such as an axial barb, extending along the axis A—A. The barb 23 is formed by a metal shaft 24 which, at its tapered free end, has lugs 25 intended to hold the barb in the flesh after it has penetrated.

The barb 23 is fixed to the head 20 along the axis of the end-fitting 19. It is, for example, screwed into a threaded hole formed axially in the end-fitting 19.

In addition, the rod 8 includes an axially formed passage 26 intended for the main span of the barb 23 to run through. As shown in FIGS. 1 to 4, the passage 26 is formed by a transverse orifice made in the thickness of the rod 8.

The jaw-pieces 9 internally have, in their region connecting with the arms 13, axial channels 27A for accommodating the barb 23 when the forceps is closed. Likewise, axial channels 27B are provided on the arms 13 in their regions connecting with the protuberances 16.

In order to assemble the device, the two jaw-pieces 9 are suitably placed on the head 20, then they are inserted into the component 3 and, finally, the rod 8 is fitted.

Figure 3:
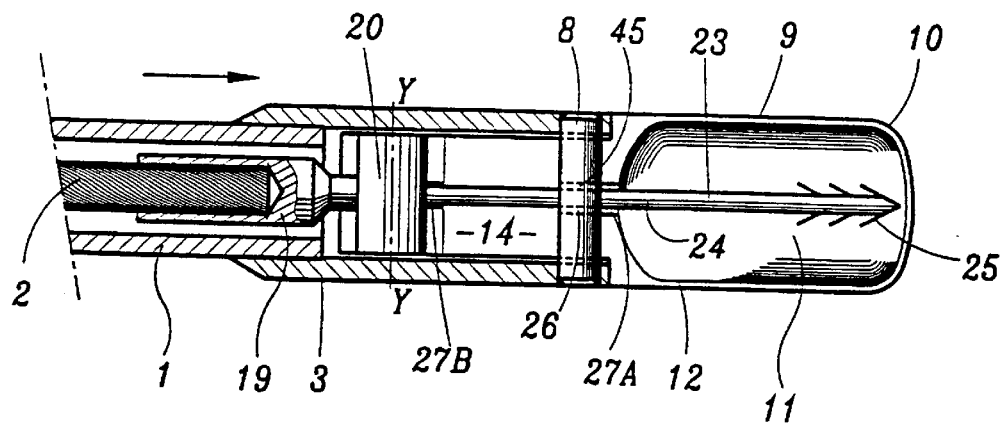
FIG. 3 is an axial sectional view of the device in an axial plane of the rod.

When, starting from the closed forceps position shown in FIGS. 2 and 3, the cable is pushed upward, in the direction of the arrow, the head 20 pushes the two jaw-pieces 9 upward so that the surfaces 14, which slide on the rod 8, rapidly produce a ramp effect which tends to move the two arms 13 apart, causing them to pivot about the head 20, while still keeping the two excrescences 16 assembled around the head because these ends remain guided in the square passage 4.

This rocking movement of the arms is progressively allowed because of the inclination of the external surface 15 of the arms, which avoids jamming and guides the arms as they rise above the rims 7. At the end of travel, the movement is stopped by the presence of the rod and the two jaw-pieces 9 are in the position of maximum opening represented in FIG. 4.

The jaw-pieces are closed by maneuvering the cable 2 in the opposite direction to that of the arrow.

The length of the barb 23 is tailored so that, when the jaw-pieces of the forceps are closed, the free end of the barb arrives substantially at the front end of the jaw-pieces while allowing the barb to be accommodated fully inside the forceps.

Figure 4:
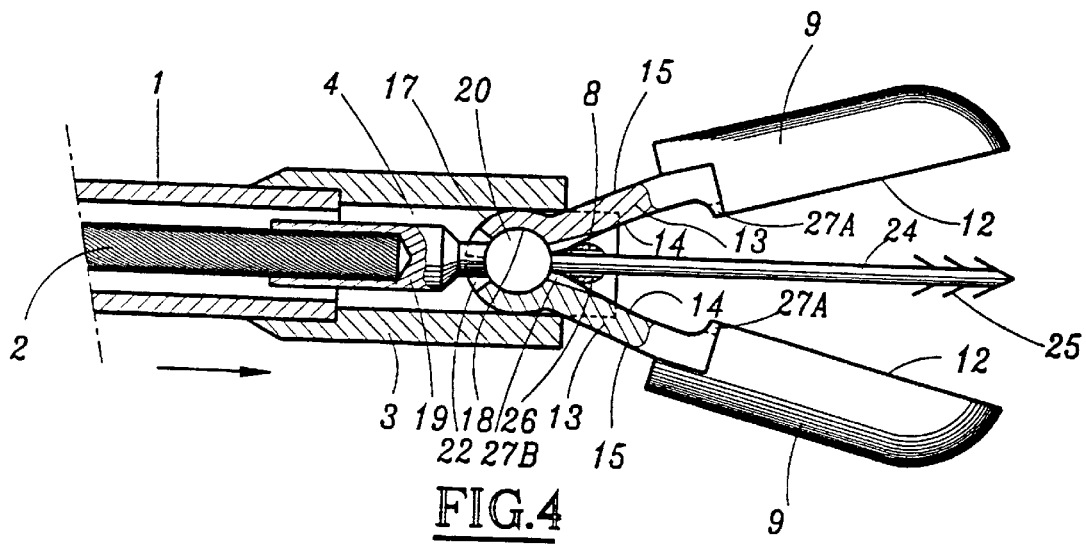
FIG. 4 is a view similar to FIG. 2 in a position in which the jaw-pieces are apart.

Conversely, when the forceps is in the open position, as shown in FIG. 4, the end-fitting 19 being pushed forward toward the rod 8, the free end of the barb 23 protrudes by a few millimeters in relation to the ends of the jaw-pieces. Thus, in this position, the barb can penetrate the flesh of the organ from which the biopsy is to be taken.

After the barb has been driven in, when the operator pulls the cable 2 inside the sheath 1, the barb, firmly anchored by the lugs 25 inside the flesh of the organ, pulls part of the latter between the jaw-pieces 9. The sliding of the barb 23 is made possible by the presence of the passage 26. Under the action of the tension on the cable 2, the jaw-pieces 19, by coming together, cut the flesh beyond the free end of the barb. Thus, the part of the organ retained around the barb is detached from the organ and is held trapped in the cavities 11 of the jaw-pieces.

It will be understood that a biopsy forceps has thus been produced which is composed of a very small number of elements and whose mechanical simplicity makes it possible to eliminate virtually any risk of failure. Furthermore, the mechanical forces on such a forceps, which may be highly miniaturized, are perfectly distributed.

In addition, in the embodiment of FIGS. 1 to 4, after the cylindrical head 20 has been engaged between the excrescences 16, the axial guidance without rotation of the head 20 is controlled by the contact of the cylindrical surfaces 17 on the plane walls delimiting the central passage 4. The complementary cylindrical shapes of the head 20 and of the channels 18 provide the articulation of the jaw-pieces.

In addition, the biopsy-forceps head described here is short in the axial direction due to the simplicity of its construction. Thus, it can move in guide tubes having small radii of curvature without any risk of jamming.

As a variant, the forceps head may have asymmetrical jaw-pieces, one of which carries, for example, a single tooth and the other of which carries two teeth delimiting a space for receiving the single tooth of the complementary jaw-piece when the forceps is closed.

FIG. 5 shows another embodiment of the device described with reference to FIGS. 1 to 4.

The alternative embodiment of FIG. 5 differs from that of FIGS. 1 to 4 only as regards the transverse rod and the shape of the excrescences 16 and, in particular, the shape of the concave hollow cavities which they delimit.

In this embodiment, the two jaw-pieces 9 are identical. The excrescence 16 of each of them is formed by an eye 28 with cylindrical outer sidewall. Each eye internally delimits a hollow cylindrical conduit 29. The common axis of the eyes extends parallel to the generatrices of the internal surfaces 14, that is to say parallel to the rod 8. Each eye extends at one end of an arm 13 in the extension of a corresponding side face. The axial length (along the axis of the rod 8) of each eye is substantially equal to one-third of the width of the arm 13.

In the assembled instrument, the cylindrical ends of the head 20 are accommodated in the hollow cylindrical conduits 29 of the eyes, which provides the articulation of the jaw-pieces relative to the end-fitting 19.

According to yet another alternative, not shown, the protuberance 16 of each arm is formed over half the width of each arm 13 by an end eye extended by a channel-shaped section similar to the channel 18 of FIGS. 1 to 4.

In this embodiment, the transverse member 8 is formed by two coaxial half-rods 40A, 40B, each carried by an extension 5. The passage is then delimited by the gap formed between the two half-rods 40A, 40B.

FIG. 6 shows an alternative embodiment of the end-fitting 19 which can be employed in a forceps as described with reference to FIGS. 1 to 4, on the one hand, and FIG. 5, on the other hand.

The head 20, of substantially cylindrical shape in the preceding figures, is replaced in FIG. 6 by a head 30 which is not cylindrical but axisymmetric about the axis Y—Y which extends perpendicular to the axis A—A of the forceps. In FIG. 6, the head 30 has the shape of an olive and has two narrowed ends. The head 30 is axisymmetric about the axis Y—Y and is generated by an arc of a circle.

With a head as shown in FIG. 6, the concave hollow cavities carried by the jaw-pieces 9, and formed by the channels 18 or the axisymmetric conduits 29, have profiles complementary to that of the head 30. Thus, the channels 18 are generated not by a straight generatrix, but by an arc of a circle similar to the arc defining the wall of the head 30. Similarly, the passages 29 have a cross section decreasing progressively toward the outside of the forceps and are generated by an arc of a circle with similar curvature to the arc of a circle generating the head 30.

It will be understood that the head 30 may assume very different profiles, provided that it is generally axisymmetric about the axis Y—Y extending perpendicular to the axis A—A of the forceps. The curve generating the axisymmetric head 30 is thus arbitrary.

The internal profile of the channels 18 or of the conduits 29 is tailored accordingly and has an axisymmetric shape complementary to that of the head carried by the end-fitting 19.

In all cases, the elongate shape of the head about which the jaw-pieces are articulated guarantees that they are axially fixed in relation to the component 3.

As a variant, not shown, the head is spherical and forms a ball-and-socket joint. In this case, the excrescences 16 have a substantially complementary spherical cavity for accommodating the head. The jaw-pieces are then free to rotate in relation to the axis of the end-fitting 19.

Figure 7:
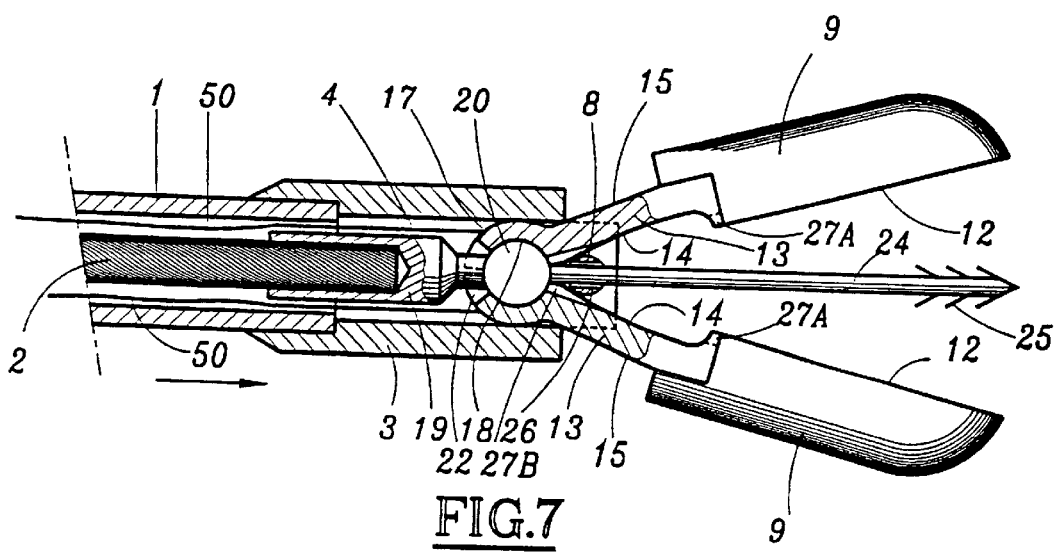
FIG. 7 is a view similar to that in FIG. 4 of another embodiment of the invention.

According to yet another alternative embodiment of the device, shown in FIG. 7, the sheath 1 and, in particular, its outer surface, are made of an electrically insulating material. Furthermore, the two jaw-pieces 9 are made of an electrically conductive material and have means for connection to a source of potential. These connection means are, for example, formed by insulated conducting wires 50, one end of which is welded to the jaw-pieces and the length of which extends over the length of the sheath 1. These wires extend through the inter-wall space delimited between the sheath 1 and the cable 2.

When the device is being used, the establishment of a potential difference between, on the one hand, the metal jaw-pieces in contact with the patient's flesh and, on the other hand, an electrode applied to the patient's body makes it possible to coagulate the flesh in the part in contact with the jaw-pieces of the forceps.

As a variant, the two jaw-pieces are electrically insulated from each other and are connected to sources of different potentials, so that a potential difference can be established between the two jaw-pieces. Such a device also makes it possible to coagulate the flesh clamped between the two jaw-pieces.

In this case, the end-fitting 19 and the rod 8 are made of an insulating material such as ceramic.

Furthermore, only a limited area of the jaw-pieces entering into contact with the patient's flesh may be electrically conductive, the rest of the structure of the jaw-pieces being made of an insulating material.

Figure 8:
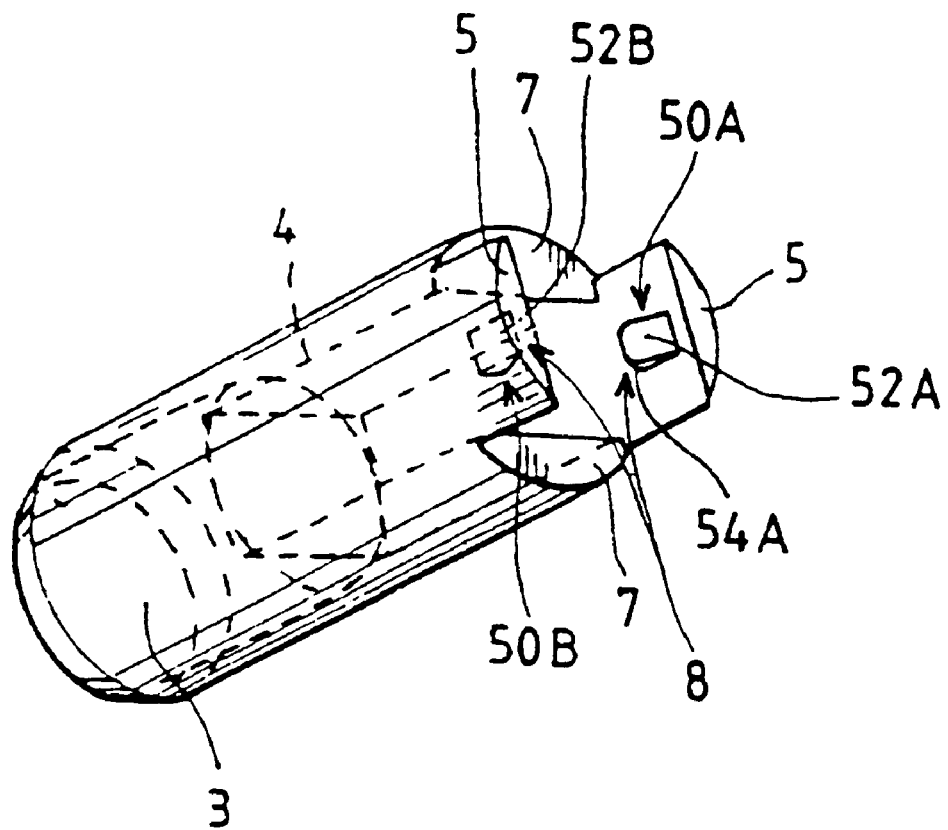
FIG. 8 is a perspective view of an alternative embodiment of the tubular element forming the body of the forceps.

FIG. 8 shows an alternative embodiment of the tubular element denoted by the general reference 3.

In this embodiment, the transverse member denoted by the general reference 8 is formed by two protuberances 50A, 50B projecting into the square cross-sectional central passage 4.

The protuberances 50A, 50B are integral with the tubular element 3. They are carried by the facing surfaces of the extensions 5. They are located slightly above the plane defined by the two lowermost edges of the crenels 7.

The protuberances 50A, 50B are symmetrical with respect to the axis of the forceps. They each delimit a ramp 52A, 52B, the normal of which is directed toward the front of the forceps. The ramps 52A, 52B are each defined laterally by flanks extending parallel to the axis of the forceps.

At its rear end, in its region of maximum height, each protuberance is bordered by a semicylindrical side surface denoted 54A, 54B, the generatrix of which extends perpendicular to the axis of the forceps. The semicylindrical side surfaces 54A, 54B form shoulders defining cam surfaces for the internal surfaces 14 of the arms. The height of the surfaces 54A, 54B is substantially equal to 0.1 mm in the case of a forceps whose external diameter is 2 mm.

In a biopsy forceps comprising the tubular element 3, the other members are identical to those described with reference, for example, to FIG. 1.

In order to assemble such a forceps, the arms 13 are engaged on either side of the head 20. The head 20 and the convex end excrescences 16 of the arms are inserted into the passage 4 from the front end of the tubular element 3. During their insertion, the arms 13 enter into contact with the ramps 52A, 52B, which causes the extensions 5 to move apart by elastically deforming them. This deformation of the front end of the tubular element 3 thus makes it possible to insert the end excrescences 16.

After the arms 13 have entered the passage 4 sufficiently, the protuberances 50A, 50B are accommodated between the internal surfaces 14 of the arms. The protuberances then, on the one hand, retain the arms 13 partially inside the passage 4 and, on the other, move the jaw-pieces away from each other when the end-fitting 19 is moved forward.

It can be seen that, with a tubular element 3 as represented in FIG. 8, the jaw-pieces are moved away from each other by the integral protuberances, which reduces the total number of components of the forceps and allows the latter to be assembled more rapidly.

In addition, as in the previous embodiments, a passage is formed between the two protuberances, which allows an auxiliary tool to be put between the two jaw-pieces.

Advantageously, the tubular element represented in FIG. 8 may be used with an end-fitting 19 whose head is spherical and forms a ball-and-socket joint. In this case, the excrescences 16 have a spherical cavity for accommodating the head.

It will be understood that, with a forceps according to the invention, which does not have a link or other complex mechanism projecting in certain positions out from the generally cylindrical envelope of the forceps, it is possible for the insulating sheath 1 to be arranged far in front of the tubular element 3, so that the sheath fully covers the latter and only the conductive jaw-pieces are exposed.

Finally, according to yet another variant, the jaw-pieces 9 have reliefs on their outer side face, in particular hooks or ridges intended for gripping hollow organs. Such a device is, in particular, intended for removing catheter debris from a vein or an artery. The device then operates as a retractor and makes it possible to grip hollow objects when the jaws, following insertion in the closed state, are moved away from each other inside it and the reliefs are in contact with the internal surface of the hollow object.

What is claimed is:

1. A forceps instrument comprising:

a sheath having a first end;

an elongated maneuvering element slidably disposed in the first end of said sheath;

said sheath having an axis;

two jaw-pieces;

at least one of said jaw-pieces being movable away from and toward the other of said jaw-pieces when said maneuvering element slides axially in the first end of the sheath, wherein said jaw-pieces have, in an extension of a part of the jaw-pieces, an arm extending progressively toward the axis of the sheath so as to form a first, internal, inclined surface extending progressively toward the axis and facing the latter, a second, external, inclined surface extending progressively toward the axis and facing an internal surface of the sheath;

said arm having a convex excrescence which is slidable substantially against said internal surface of the sheath;

said excrescence having a concave hollow cavity facing the axis;

said sheath having, near its end beyond which said jaw-pieces extend, a transverse element against which said internal surface of said arm slides;

said elongate maneuvering element terminating in a head housed in said concave hollow cavity so that, when said elongate maneuvering element is moved toward said first end of the sheath, it pushes said jaw-pieces back beyond the first end of the sheath, thus causing the internal surface of said arm, which slides over said transverse element, to pivot by a ramp effect, moving the at least one jaw-piece of the jaw-pieces away from the other jaw-piece, said movement away being permitted by the inclination of said external surface which protrudes from the internal surface of the first end of the sheath, said excrescence of the arm pivoting, during this movement, about said head while still being guided in said sheath, reverse movement of the maneuvering element causing the jaw-pieces to move closer by a reverse movement; and said transverse element including a passage having an axis substantially parallel to the axis of the sheath for accommodating an auxiliary tool between the two jaw-pieces.

2. The forceps instrument according to claim 1, wherein the instrument is of the biopsy-forceps type.

3. The forceps instrument according to claim 2, wherein the sheath is rigid.

4. The forceps instrument according to claim 3, wherein the elongated maneuvering element is a cable.

5. The forceps instrument according to claim 4, wherein said transverse element is a rod.

6. The forceps instrument according to claim 1, wherein said transverse element includes an interruption forming said passage, said transverse element being formed by two coaxial half-rods carried by the first end of the sheath.

7. The forceps instrument according to claim 1, wherein said transverse element includes an orifice forming said passage, which orifice extends substantially perpendicularly to the axis of the transverse element.

8. The forceps instrument according to claim 1, wherein said transverse element has two protuberances which are integral with said sheath and project from the internal surface of the first end of the sheath.

9. The forceps instrument according to claim 8, wherein each protuberance delimits a ramp whose normal is directed toward the first end of the sheath, each ramp being extended by a shoulder to permit sliding of said internal surface of said associated arm.

10. The forceps instrument according to claim 1, further comprising an auxiliary tool passing through the passage of the transverse element.

11. The forceps instrument according to claim 10, wherein said head is extended along the axis of the sheath by said auxiliary tool, said tool being secured to said head, said tool being translationally movable in said passage of the transverse element when the maneuvering element is moved in the sheath.

12. The forceps instrument according to claim 11, wherein said auxiliary tool comprises a rigid shaft tapered at its end and forming a barb.

13. The forceps instrument according to claim 12, wherein the shaft is screwed into a threaded hole in said head.

14. The forceps instrument according to claim 1, wherein said outer surface of said jaw-pieces have reliefs therein for gripping a hollow object when said jaw-pieces are moved apart in said hollow object.

15. The forceps instrument according to claim 1, wherein the maneuvering element and the sheath include a mechanism acting, in turn, to respectively, hold one of, and move the other of, the maneuvering element and the sheath in position with respect to an organ to be treated.

16. The forceps instrument according to claim 1, wherein said jaw-pieces are electrically insulated from an outer surface of the sheath, and in that said jaw-pieces have a device for connection to a source of potential.

17. The forceps instrument according to claim 16, wherein the two jaw-pieces are electrically insulated from one another and have a device for connection to sources of different potentials.

18. The forceps instrument according to claim 1, wherein said head and said concave hollow cavity are spherical and form a ball-and-socket joint for the articulation of the jaw-pieces.

19. The forceps instrument according to claim 1, wherein said jaw-pieces comprise jaws.

* * * * *